(12) United States Patent
Klucker et al.

(10) Patent No.: US 8,703,095 B2
(45) Date of Patent: Apr. 22, 2014

(54) IMMUNO-ADJUVANT EMULSION

(75) Inventors: Marie-Francoise Klucker, Caluire et Cuire (FR); Francois Dalencon, Lyons (FR); Patricia Probeck-Quellec, Lyons (FR)

(73) Assignee: Sanofi Pasteur S.A., Lyon (FR)

( * ) Notice: Subject to any disclaimer, the term of this patent is extended or adjusted under 35 U.S.C. 154(b) by 1211 days.

(21) Appl. No.: 11/483,358

(22) Filed: Jul. 7, 2006

(65) Prior Publication Data

US 2007/0014805 A1 Jan. 18, 2007

Related U.S. Application Data

(60) Provisional application No. 60/706,707, filed on Aug. 9, 2005, provisional application No. 60/713,274, filed on Sep. 1, 2005.

(30) Foreign Application Priority Data

Jul. 7, 2005 (FR) ..................................... 05 07240
Aug. 4, 2005 (FR) ..................................... 05 08310

(51) Int. Cl.
*A61K 9/107* (2006.01)

(52) U.S. Cl.
USPC ... 424/1.11; 424/1.65; 424/278.1; 424/283.1; 424/522; 424/524

(58) Field of Classification Search
USPC .......... 424/1.11, 1.65, 278.1, 283.1, 522, 524
See application file for complete search history.

(56) References Cited

U.S. PATENT DOCUMENTS

| | | | |
|---|---|---|---|
| 3,384,544 A * | 5/1968 | Walton et al. | 424/237.1 |
| 5,980,912 A * | 11/1999 | Podolski et al. | 424/278.1 |
| 6,299,884 B1 | 10/2001 | Van Nest et al. | |
| 6,544,518 B1 | 4/2003 | Friede et al. | |
| 6,787,523 B1 | 9/2004 | Schenk | |
| 2003/0022852 A1 | 1/2003 | Nest et al. | |
| 2003/0060559 A1 | 3/2003 | Oliviere et al. | |
| 2005/0079185 A1* | 4/2005 | Parisot et al. | 424/184.1 |
| 2007/0270507 A1* | 11/2007 | Weiss et al. | 516/53 |

FOREIGN PATENT DOCUMENTS

| WO | WO 2005/009462 A2 | 2/2005 |
|---|---|---|
| WO | 2006113373 | 10/2006 |

* cited by examiner

*Primary Examiner* — Ali Soroush
(74) *Attorney, Agent, or Firm* — McDonnell Boehnen Hulbert & Berghoff LLP

(57) ABSTRACT

The invention relates to an oil-in-water adjuvant emulsion which comprises at least:
squalene,
an aqueous solvent,
a polyoxyethylene alkyl ether nonionic surfactant,
a hydrophobic nonionic surfactant,
which emulsion is thermoreversible, and wherein 90% of the population by volume of the oil drops has a size less than 200 nm.

The invention also relates to a process for preparing an immunogenic composition according to which at least one vaccine antigen is mixed with an oil-in-water emulsion, wherein the oil-in-water emulsion is obtained by means of a temperature-variation phase-inversion process.

27 Claims, No Drawings

IMMUNO-ADJUVANT EMULSION

This application claims the benefit of U.S. provisional application 60/706,707, filed Aug. 9, 2005, and U.S. provisional application 60/713,274, filed Sep. 1, 2005.

The present invention relates to the field of vaccines; more particularly, the invention relates to the field of vaccines comprising an adjuvant emulsion.

Many vaccines which contain one or more adjuvants exist in the prior art. U.S. Pat. No. 6,299,884 discloses in particular an adjuvant formulation comprising an oil-in-water emulsion, in which the size of the oil droplets is between 100 and 1000 nm. This emulsion is obtained by means of a high pressure homogenizer (microfluidizer), in the course of a manufacturing process using high mechanical energies in order to obtain shear forces that are sufficiently great to reduce the size of the oil drops. According to this teaching, while the minimum value of the size range of the drops obtained is 100 nm, the mean value is much higher and is, at best, in the region of 170 nm, more generally in the region of 500 nm.

It is desirable to have available a formulation that is an alternative to that proposed in that patent, and that can be obtained by means of a simpler process (not requiring any specific shear technology) that is a low-energy process while at the same time being reproducible and completely reliable; in addition, the adjuvant formulation must make it possible to effectively adjuvant vaccines, by making it possible in particular to increase the immune response obtained or to decrease the dose of antigen present, while at the same time exhibiting no sign of toxicity that would be detrimental to its completely safe administration.

To achieve this aim, the present invention provides an oil-in-water adjuvant emulsion which comprises at least:
  squalene,
  an aqueous solvent,
  a polyoxyethylene alkyl ether hydrophilic nonionic surfactant,
  a hydrophobic nonionic surfactant,
wherein the emulsion is thermoreversible and wherein 90% of the population by volume of the oil drops has a size less than 200 nm.

According to the invention, such an emulsion can be obtained by means of a phase inversion temperature process, which provides a very large advantage from an industrial point of view. Such a process provides all the guarantees of safety and of profitability necessary for the pharmaceutical industry. In addition, by virtue of this process, it is possible to obtain a monodisperse emulsion, the droplet size of which is very small, which renders the emulsion thus obtained particularly stable and readily filterable by means of sterilizing filters, the cutoff threshold of which is 200 nm.

According to a particular characteristic, 90% of the population by volume (or d90) of the oil drops has a size less than 160 nm, and even less than 150 nm.

According to a particular embodiment of the invention, the emulsion according to the invention also comprises an alditol; this makes it possible to obtain a phase inversion at a temperature below that which would be necessary for the same composition not containing any alditol, which makes it possible to reduce the production costs and also the risks of thermal denaturation of the constituents of the emulsion.

According to a particularly advantageous embodiment, the hydrophobic nonionic surfactant of the invention is a sorbitan ester or mannide ester surfactant. Such surfactants have the advantage of being able to be used entirely safely in injectable solutions.

According to a particular embodiment of the invention, the emulsion also comprises an alkylpolyglycoside and a cryoprotective agent such as a sugar, in particular dodecylmaltoside and/or sucrose.

Thus, it is possible to obtain a lyophilizable emulsion which, after lyophilization and reconstitution, recovers its properties, in particular particle size properties, i.e. the lyophilized and then reconstituted emulsion is still monodisperse and consists of oil droplets, 90% of the population by volume of which has a size of less than 200 nm. This is particularly important for the field of vaccines which must sometimes, for reasons of stability (either of certain antigens, or of certain adjuvants), be conserved in lyophilized form.

A subject of the invention is also a process for preparing an immunogenic composition according to which at least one vaccine antigen is mixed with an oil-in-water emulsion, wherein the oil-in-water emulsion is obtained by means of a phase-inversion temperature process.

According to one embodiment of the invention, the oil-in-water emulsion is prepared by cooling a water-in-oil inverse emulsion which comprises at least:
  squalene,
  an aqueous solvent,
  a polyoxyethylene alkyl ether hydrophilic nonionic surfactant,
  a hydrophobic nonionic surfactant.

By virtue of such a process, which is very advantageous from an industrial point of view, a stable immunogenic composition is obtained which is very effective even at a very low dose of antigens.

In addition, by virtue of the preparation process used, the droplets of oil of the emulsion all have virtually the same size, which is very small; in fact, when the size distribution curve is represented for the drops obtained, it is noted that a monodisperse emulsion is obtained, with a very tight Gaussian-type distribution, centered around a single low value, generally around 80-90 nm.

According to a particular embodiment of the process according to the invention, the water-in-oil inverse emulsion is obtained by mixing squalene, an aqueous solvent, a polyoxyethylene alkyl ether hydrophilic nonionic surfactant, and a hydrophobic nonionic surfactant, in order to obtain, first of all, a coarse oil-in-water emulsion, and this emulsion is then heated to at least the phase-inversion temperature in order to obtain the inverse emulsion. This way of processing is advantageous because the different components of the emulsion are submitted to a high temperature only during a short time.

According to another embodiment of the process according to the invention, the water-in-oil inverse emulsion is prepared by:
  separately heating (a) the aqueous phase comprising the aqueous solvent and the polyoxyethylene alkyl ether nonionic surfactant and (b) the oily phase comprising the squalene and the hydrophobic surfactant, each to a temperature less than the phase inversion temperature, or one to a temperature less than the phase inversion temperature and the other to at least the phase inversion temperature
  mixing the pre-heated aqueous and oily phases, and
  if the temperature of the mixture is less than the phase inversion temperature, heating the mixture to at least the phase inversion temperature.

According to a particular embodiment of the invention, each of the aqueous and oily phases is heated separately, before mixing, to a temperature at least equal to the phase-inversion temperature. Thus, when the 2 phases are mixed, the emulsion produced will be an inverse emulsion, which will be cooled in order to obtain an oil-in-water emulsion.

According to a particular embodiment, the preparation process according to the invention also comprises a lyophilization step. Thus, the process according to the invention can be used for the preparation of immunogenic compositions comprising antigens which must be conserved in lyophilized form for reasons of stability.

Many other advantages of the present invention will become apparent in the course of the following description.

For the purpose of the invention, the term "oil-in-water emulsion" is intended to mean a dispersion of an oily phase in an optionally buffered aqueous phase which may comprise either water or a saline solution. According to a particular embodiment of the invention, the aqueous phase of the emulsion consists of a buffer, such as Dulbecco's phosphate buffered solutions (D-PBS, without calcium or magnesium).

The term "adjuvant emulsion" is intended to mean an immunoadjuvant emulsion, i.e. an emulsion capable of modifying the response induced by the immune system when administered in combination with an antigen compared to the response to the antigen obtained in the absence of the emulsion, it being possible for this immune system response to be reflected by antibody production or by activation of certain cells, in particular antigen-presenting cells (for example, dendritic cells), T lymphocytes and B lymphocytes. This cellular activation can be demonstrated by the presence of activation markers at the surface of the cells or by the release of cytokines. The modification of the immune response induced by the adjuvant emulsion may be quantitative in nature, i.e. an increase in the induced response is obtained, or qualitative in nature, i.e. a response that is different in nature or has a different orientation is obtained, or else an additional response is obtained. The term "adjuvant emulsion" is also intended to mean an emulsion that makes it possible to reduce the amount of antigens administered for the same induced response.

For the purpose of the present invention, the term "immunogenic composition" is intended to mean a composition comprising at least one antigen, that can be administered to humans or to animals in order to induce an immune system response. This response can be a humoral response (production of antibodies) or a cellular response (proliferation and/or activation of immune cells). The immunogenic composition may be a composition for prophylactic purposes or for therapeutic purposes, or else both. The immunogenic composition obtained according to the invention can be administered via any of the routes normally used or recommended for vaccines: parenterally or mucosally, and can be in various forms, in particular a liquid or lyophilized form. It can be administered by means of a syringe or by means of a needle-free injector for intramuscular, subcutaneous or intradermal injection, or by means of a nasal spray.

For the purpose of the present invention, the term "antigen" is intended to mean any antigen that can be used in a vaccine, whether it involves a whole microorganism or a subunit antigen, regardless of its nature; the antigen may in fact be a peptide, a protein, a glycoprotein, a polysaccharide, a glycolipid, a lipopeptide, etc.

The adjuvant emulsion according to the invention is particularly suitable for viral antigens; particularly good results have in fact been obtained with antigens of the human cytomegalovirus, of the human immunodeficiency virus, and of the flu virus.

As regards the flu virus antigens, it is possible to use antigens that come from a single viral strain, or from a mixture of various strains. It is possible to use antigens derived from viruses cultured conventionally on eggs, or on cells. By means of the invention, it has been noted that whether for a single strain or for a mixture of strains, it is possible to obtain a satisfactory response of the immune system while at the same time very substantially reducing the amount of antigens present in the vaccine dose. This may be of particularly great value in the case of the preparation of a vaccine against a flu pandemic, where it must be possible to produce, in a very short period of time, very large amounts of vaccine doses.

According to the invention, the oil-in-water emulsion comprises squalene, which is an oil initially originating from shark liver; it is an oil whose empirical chemical formula is $C_{30}H_{50}$, comprising 6 double bonds; this oil is metabolizable and has qualities that allow it to be used in an injectable pharmaceutical product. Squalene of plant origin, extracted from olive oil, also exists. Good results have in particular been obtained using the squalene provided by the company Fluka, which is of animal origin. The amounts of squalene used for the preparation of a concentrated emulsion are advantageously between 5 and 45%; this concentrated emulsion is subsequently diluted during the preparation of the immunogenic compositions so as to prepare immunizing doses in which the amount of squalene is between 0.5 and 5%. This dilution can be carried out by simple mixing of the adjuvant emulsion according to the invention and the suspension comprising the antigen.

According to the invention, the emulsion comprises a nonionic hydrophilic surfactant, the hydrophilic/lipophilic balance, or HLB, value of which is greater than or equal to 10, and which belongs to the chemical group of polyoxyethylene alkyl ethers (PAEs), also called polyoxyethylenated fatty alcohol ethers, or n-alcohol polyoxyethylene glycol ethers. These nonionic surfactants are obtained by chemical condensation of a fatty alcohol and ethylene oxide. They have a general chemical formula $CH_3-(CH_2)_x-(O-CH_2-CH_2)_n-OH$, in which n denotes the number of ethylene oxide units (typically 10-60), and (x+1) is the number of carbon atoms in the alkyl chain, typically 12 (lauryl(dodecyl)), 14 (myristyl(tetradecyl)), 16 (cetyl(hexadecyl)), or 18 (stearyl(octadecyl)), so x is in the range of from 11 to 17. Polyoxyethylene alkyl ethers tend to be mixtures of polymers of slightly varying molecular weights. Accordingly, the emulsions of the invention will comprise a mixture of polyoxyethylene ethers. Furthermore, because polyoxyethylene alkyl ethers are mixtures, when a particular polyoxyethylene ether is recited herein for use in an emulsion, it will be understood that it is the primary but not necessarily the only polyoxyethylene alkyl ether present in the emulsion. At least 2 systems of nomenclature are used to describe these materials. One nomenclature refers to the approximate polymer length in oxyethylene units; another refers to the average molecular weight of the polymer chain.

The polyoxyethylenated fatty alcohol ethers that are suitable for the subject of the invention can be in a form which is liquid or solid at ambient temperature. Among solid compounds, preference is given to those which dissolve directly in the aqueous phase or which do not require substantial heating.

Insofar as the number of ethylene oxide units is sufficient, polyoxyethylenated ethers of lauryl alcohol, myristyl alcohol, cetyl alcohol, oleyl alcohol and/or stearyl alcohol are particularly suitable for the subject of the invention. Some of them can be found among products known under the trade names Brij® for the products sold by the company ICI America's Inc., Eumulgin® for the products sold by the company Cognis, or Simulsol® for the products sold by the company Seppic.

An emulsion which is particularly preferred according to the invention contains, as hydrophilic nonionic surfactant, a polyoxyethylene alkyl ether chosen from the group consisting of ceteareth-12 (sold under the name Eumulgin® B1), ceteareth-20 (Eumulgin® B2), steareth-21 (Eumulgin® S21), ceteth-20 (Simulsol® 58 or Brij® (58), ceteth-10 (Brij® 56), steareth-10 (Brij® 76), steareth-20 (Brij® 78), oleth-10 (Brij® 96 or Brij® 97) and oleth-20 (Brij® 98 or Brij® 99). The number attributed to each chemical name corresponds to the number of ethylene oxide units in the chemical formula.

Good results have been obtained with the product BRIJ® 56. A compound that is particularly suitable and preferred because of its semi-synthetic origin is polyoxyethylene (12) cetostearyl ether, provided by the company Cognis under the name Eumulgin™ B1. This product is a mixture of 2 polymers: $CH_3(CH_2)_{15}(OCH_2CH_2)_{12}OH$ and $CH_3(CH_2)_{17}(OCH_2CH_2)_{12}OH$.

According to the invention, the adjuvant emulsion also comprises a hydrophobic nonionic surfactant, which must be pharmaceutically acceptable; among surfactants that are suitable in this regard, mention may be made of sorbitan ester or mannide ester surfactants; the sorbitan ester surfactants are obtained by reaction of a fatty acid and of a mixture of partial esters of sorbitol and its mono- and dianhydrides; this may involve a mono-, a di- or a triester, or even a mixture; they are hydrophobic surfactants for which the overall hydrophilic-lipophilic balance (HLB) is less than 9, and preferably less than 6. Some of them can be found amoung the surfactants sold by the company ICI Americas Inc. under the name Span®, or by the company Cognis under the name Dehymuls™, or by the company ICI under the name Arlacel™; as examples of surfactants that are particularly suitable, mention may be made of the sorbitan monooleate sold under the name Dehymuls SMO™ or Span®80. Among the mannide ester surfactants, mention may be made of the mannide monooleate sold by the company Sigma, or by the company Seppic under the name Montanide 80™.

By virtue of the selection of these specific surfactants among all the surfactants proposed in the prior art for preparing emulsions, it has now been found that an oil-in-water adjuvant emulsion can very advantageously be produced using a phase-inversion temperature process. To this end, the amounts of squalene and of each of the surfactants used are advantageously chosen so as to obtain a mixture for which the phase diagram contains a zero mean curvature phase (microemulsion or lamellar phase type) for which the interfacial tensions are extremely low.

In the case of the use of squalene, it has been noted that the emulsions obtained are stable and monodisperse and have a very small oil droplet size (d90 less than 200 nm), when the overall HLB value for the various surfactants used is between 8.5 and 10, and more particularly between 8.6 and 9.6. To determine the respective concentrations of hydrophilic and hydrophobic surfactants in the composition of the emulsion, the following formula can be used:

$HLB_m = HLB_o \times P + HLB_{pae}(1-P)$ in which, $HLB_m$ corresponds to the HLB of the mixture, which is preferably between 8.5 and 10, and more particularly between 8.6 and 9.6

$HLB_o$ corresponds to the HLB of the hydrophobic surfactant,

P corresponds to the percentage in weight of the hydrophobic surfactant in the mix comprising the hydrophobic surfactant and the polyoxyethylene alkyl ether, $HLB_{pae}$ corresponds to the HLB of PAE.

In particular, it has been noted that it is of interest to use an amount of squalene between 5 and 45%, in order to get an emulsion which can be inverted by heating to a temperature inferior to 95° C.

For such an emulsion, it is possible to use a polyoxyethylene alkyl ether at a concentration of between 0.9 and 9% and a hydrophobic nonionic surfactant at a concentration of between 0.7 and 7%, the rest being constituted by an aqueous solvent.

According to a particular embodiment of the invention, the immunogenic composition also comprises an alditol such as, in particular, glycerol, erythritol, xylitol, sorbitol or mannitol. Good results have in particular been obtained with the mannitol sold by the company Roquette Frères. The amounts of alditol used in the preparation process can range between 1 and 10%, and more particularly between 2 and 7.

According to a particular embodiment of the invention, the adjuvant emulsion also comprises a cryoprotective agent which makes it possible to lyophilize the emulsion obtained; among the cryoprotective agents, sugars are particularly preferred, and especially sucrose. In addition, the emulsion according to the invention can comprise an alkylpolyglycoside, which is a surfactant with a sugar head; it may in particular be sodium decyl-D-galactoside uronate, or, according to a preferred embodiment, dodecyl-β-maltoside available from the company Roche.

By virtue of the process for preparing the emulsion according to the invention by phase inversion temperature, a direct oil-in-water emulsion, the size of the oil droplets of which is very homogeneous, is very readily and very reproducibly obtained: the d90 value (by volume) is less than 200 nm, preferably less than 150 nm, and even close to 100 nm, while the d50 value is less than 100 nm, or even 90 nm. For most of the emulsions prepared according to the process of the invention, the d50 were around 80 nm with d90 around 100 nm. It is thus possible to perform a sterilizing filtration of the emulsion obtained, on the condition that the latter is sufficiently diluted.

Such emulsions in which the size of the drops is homogeneous and very small are stable over time. An emulsion prepared according to the invention and stored at 4° C., retained, after 2 years, a monodisperse profile with a d50 value of 90 nm and a d90 value of 116 nm, demonstrating that the emulsion is very highly stable.

The size of the drops can be measured by various means, and in particular by LASER diffraction particle sizes, such as the Beckman Coulter devices of the LS range (in particular the LS230). The principle of measurement of these devices is based on analyzing the intensity of the light scattered by the particles as a function of the angle (large, medium and small angle detectors) when the sample is illuminated by a LASER beam. This analysis is carried out by means of mathematical models chosen according to the size and the nature of the material used. In the case of the measurement of the size of submicronic particles, it is necessary to apply a specific optical model (Mie theory) taking into account the refractive indices of the sample (here, 1.495 for squalene) and of its medium (here, 1.332 for water); it is also necessary to be capable of detecting the weak intensities emitted by the very fine particles, which requires an additional detection cell for the large-angle polarized intensity differential scattering measurement (such as the PIDS system from Coulter, which allows measurement from 40 nm). For the purposes of description of the invention, the d50 and d90 parameters mentioned in the present patent application are values by volume; the d50 value signifies the value of 50% of the population by volume of drops.

The process according to the invention can be carried out in the following way: a concentrated crude oil-in-water emulsion is prepared by incorporation of the aqueous phase (buffer solution, to which alditol is optionally added, comprising the nonionic surfactant with ethylene oxide groups) into the oily phase (squalene, and hydrophobic nonionic surfactant); or, conversely, by incorporation of the oily phase into the aqueous phase. A noncalibrated oil-in-water emulsion is then obtained, which rapidly manifests its instability. This emulsion is stirred and heated until a phase inversion is obtained, i.e. a water-in-oil emulsion is obtained. The phase inversion or transition can be monitored by conductimetry. During heating, the conductivity of the emulsion increases until the phase inversion, at which point there is a relatively sudden drop of the conductivity. The temperature at which the change in curvature that reflects the passage from one type of emulsion to another occurs is the phase inversion temperature. In reality, this temperature is rather a temperature range than a very precise point value; in fact, it may be considered that this temperature is a temperature determined to within 1 or 2 degrees so that the entire emulsion undergoes the phase inversion phenomenon. Once this phase inversion temperature has been reached, and therefore once in the presence of a water-in-oil emulsion, heating is stopped and the mixture cooled. Cooling can be carried out passively, by simply allowing the emulsion to return spontaneously to ambient temperature, or more actively, by immersing the emulsion, for example, in an ice bath. When the emulsion passes through the phase inversion temperature, the water-in-oil emulsion will invert again so as to once more give an oil-in-water emulsion in which the size of the oil droplets is this time very homogeneous and small; the emulsion obtained is then very stable. It can be stored as it is, while awaiting dilution with a solution comprising the vaccine antigen.

This emulsion is thermoreversible, which means that, if it is again brought to a temperature above the phase inversion temperature, it will once again become a water-in-oil emulsion. It has to be noted that the curves representing the conductivity as a function of the temperature are always the same, whatever the number of times the phase inversion temperature process is applied to the emulsion; the granulometric profile of the emulsions are always the same too. Advantageously according to the invention, the formulation of the emulsion is chosen so as to have a phase inversion temperature that is below 95° C., and more particularly between 45 and 80° C., and even more particularly between 50 and 65° C. This temperature range is advantageous because there is no risk of the emulsion changing state if it is stored at a relatively high temperature ($\approx 37°$ C.). Furthermore, as in the process for preparing the thermoreversible emulsion, the heating of the components should not exceed 80° C., and this contributes toward maintaining the structural integrity of the components. When the phase inversion temperature of the emulsion is high, in particular when it is greater than or in the region of 80° C., it can be useful to reduce it by adding to the composition of the emulsion an alditol, which is normally chosen from sorbitol, mannitol, glycerol, xylitol or erythritol. When the alditol is used in a concentration range of from 1 to 10% (w/w), and in particular in a concentration range of from 2 to 7% (w/w), it is possible to reduce the phase inversion temperature of the emulsion by approximately 10° C. The phase inversion temperature of the emulsion can also be reduced by replacing the aqueous phase consisting only of water with a buffered saline aqueous phase. A Tris buffer, or a phosphate buffer such as PBS or the Dulbecco PBS buffer without $Ca^{2+}$ or $Mg^{2+}$ is normally used.

Alternatives to the process that has just been described exist. Specifically, it is possible, as has just been described, to mix both the aqueous and the oil phases in order to obtain the crude emulsion which will then be heated and then cooled. Alternatively, the mixtures that have been prepared separately can be heated to a temperature slightly above the phase inversion temperature, before being combined so as to give a water-in-oil inverse emulsion, which will be cooled until the oil-in-water submicronic emulsion is obtained.

Alternatively, it is also possible to slightly heat each phase before mixing, and then heat the crude emulsion until the phase inversion is obtained before cooling.

These operations can be carried out in separate containers for a batch preparation.

It is also possible to use an on-line process.

The process for producing the emulsion on-line can consist of mixing, under hot conditions, the two aqueous and oily phases prepared separately beforehand, through a thermostatted static mixer, followed by on-line cooling through a refrigerated heat exchanger connected at the outlet of the static mixer, and then final recovery of the emulsion according to the invention in an appropriate container (flask or reactor). A static mixer consisting of a succession of mixing elements made up of cross blades inclined relative to the axis of the tube into which they are introduced was successfully used. The energy required for the mixing is provided by the pumps that transport the fluids past the mixing elements, and the mixing is carried out without any movement of the mixing elements by virtue of separating, displacing and successive combining of the constituents of the mixture.

The on-line production process is carried out in the following way: the aqueous phase (buffered solution comprising the polyoxyethylene alkyl ether) and the oily phase (squalene and hydrophobic nonionic surfactant) are prepared separately in two flasks or reactors. The two phases are heated with stirring to a temperature slightly above the phase inversion temperature. The two phases are then introduced into a thermostatted static mixer by means of 2 pumps, the flow rates of which are regulated so as to obtain the composition of the emulsion according to the invention. The water-in-oil inverse emulsion is obtained during the passage of the two phases in the static mixer. The inverse emulsion is subsequently cooled by passing it on-line through a refrigerated heat exchanger connected at the outlet of the static mixer. The water-in-oil emulsion will then invert through the refrigerated heat exchanger to give an oil-in-water emulsion, which will be collected in a flask or reactor. The characteristics of the emulsion so obtained are identical to those of the emulsion obtained by a batch process.

The adjuvant emulsion according to the invention is then used for preparing an immunogenic composition. A simple embodiment consists in mixing an aqueous solution comprising at least one vaccine antigen in an emulsion obtained according to one of the embodiments which has just been described. The immunogenic composition obtained is in the form of an oil-in-water emulsion or in the form of an oil-in-water emulsion which is thermoreversible when the amount of squalene represents by weight at least 5% of the total weight of the immunogenic composition. The aqueous solutions of the antigen can also contain mineral salts and one or more buffers, and also any other compound normally used in vaccines, such as stabilizers, preserving agents or also optionally other adjuvants.

As an alternative way, it is possible to mix the antigen with the aqueous or the oil phase before preparing the emulsion.

For the preparation of a lyophilizable emulsion, a concentrated liquid emulsion is first of all prepared, as has just been described, but preferably choosing water rather than a buffered solution as aqueous phase, and then this emulsion is diluted with a solution comprising an alditol, a sugar and an alkylpolyglycoside, for example with a solution comprising mannitol, sucrose and dodecylmaltoside.

The emulsion obtained is then divided up into samples (for example, 0.5 ml) and subjected to a lyophilization cycle, which can be carried out in the following way:
 loading of the samples at +4° C.,
 approximately 2 hours of freezing at a set temperature of −45° C.,
 14 to 19 hours of primary desiccation at a set temperature of 0° C.,
 3 hour 30 min of secondary desiccation at a set temperature of +25° C.

The emulsion obtained can then be conserved until it is used for the preparation of a vaccine composition, i.e. until it is combined with a composition comprising vaccine antigens. This step for preparing the vaccine composition can be carried out by taking up the lyophilized emulsion with an aqueous solution comprising the antigens. The vaccine composition thus obtained can subsequently be conserved in the liquid state, or can be subjected to a further lyophilization cycle in order to be conserved in the form of a lyophilisate, if the nature of the antigens allows this.

Alternatively, it is possible to directly dilute the concentrated emulsion with an aqueous solution comprising both the vaccine antigens and also the alditol, the sugar and the alkylpolyglycoside, and to subsequently subject the composition obtained to the lyophilization. Such a manner of carrying out the process implies, of course, that the antigens are antigens that are compatible with a lyophilization process.

The following examples illustrate various embodiments of the invention.

EXAMPLE 1

Preparation of an Adjuvant Emulsion According to the Invention 3.71 g of Eumulgin™ B1 and 33.9 g of a 10% solution of mannitol in PBS buffer were mixed in a beaker, and the mixture homogenized with stirring at approximately 30° C.

In another container, 2.89 g of Dehymuls™ SMO and 19.5 g of squalene were stirred magnetically.

When homogeneous phases were obtained in each of the containers, the aqueous phase was incorporated into the oily phase, which was maintained at 30° C. with stirring.

When the incorporation was complete, the crude emulsion obtained was heated until the temperature reached 58-60° C., while at the same time maintaining the stirring.

The heating was then stopped but the stirring maintained until the temperature reached ambient temperature.

An oil-in-water emulsion was then obtained, the size of the oil droplets of which was centered around 80 nm, and the composition by mass of which was as follows:
 32.5% of squalene,
 6.18% of polyoxyethylene (12) cetostearyl ether,
 4.82% of sorbitan monooleate,
 6% of mannitol.

EXAMPLE 2

Immunogenic Composition Against AIDS

Immunogenic compositions comprising a detoxified TAT III B protein as antigen were prepared. The TAT protein was detoxified by means of an alkylation reaction in an alkaline medium using iodoacetamide under the following conditions: number of micromoles of iodoacetamide=200× number of micromoles of TAT+number of micromoles of DTT. This detoxified protein and the process for preparing it are described in detail in application WO99/33346, where it is identified under the term carboxymethylated TAT.

This recombinant TAT antigen is conserved in solution, in the presence of 50 mM Tris buffer, pH 7.5, at −70° C.

The immunogenic compositions to be administered were prepared from concentrated solutions, in order to obtain immunization doses of 200 µl having the following quantitative compositions:
 for the composition having only the antigen: 20 µg of TAT in 50 mM Tris buffer, 100 mM NaCl, at pH 7.5;
 for the composition according to the invention:
  20 µg of TAT,
  5 mg of squalene
  0.75 mg of Dehymuls SMO,
  0.94 mg of Eumulgin B1,
  0.91 mg of mannitol.

Two groups of six 8-week-old female BALB/c mice were injected subcutaneously with one of the compositions prepared, in a proportion of one dose of 200 µl per mouse; the injections are given on D0 and on D21.

Blood samples were taken from the retroorbital sinus on D14 in order to assess the primary response and on D34 for the secondary response. The specific IgG1 and IgG2a titers were determined by means of standardized ELISA assays.

The mice were sacrificed on D37; their spleen s removed and the splenocytes isolated.

The results obtained regarding the humoral responses are summarized in the table below, in which the IgG titers are expressed in arbitrary ELISA units (log10).

For each group of mice, the value indicated in the table is the mean geometric titer of the values obtained for each of the mice.

| Vaccine composition | IgG1 at D14 | IgG2a at D14 | IgG1 at D34 | IgG2a at D34 | IgG1/IgG2a ratio at D34 |
|---|---|---|---|---|---|
| Tat | 2.6 | 1.2 | 4.4 | 3.0 | 25 |
| Tat + PIT | 3.5 | 2.5 | 5.7 | 5.0 | 5 |

The results obtained show that the emulsion according to the invention makes it possible to increase, overall, the humoral response and also tends to promote the type 1 T-helper response since the IgG2a response is increased more than the IgG1 response.

As regards the cellular response, it was possible to demonstrate, by ELISPOT assay after restimulation of the splenocytes removed with the recombinant TAT protein, a clear increase in the number of cells producing γ interferon when the splenocytes come from mice immunized with a preparation according to the invention (486 spots per $10^6$ cells versus 39 per $10^6$ for the preparation containing the antigen alone). Similarly, the assaying of the cytokines in the culture supernatants showed the greater secretion of both γ interferon (5028 pg/ml versus 1940 pg/ml) and Interleukin 5 (5365 pg/ml versus 2394 pg/ml).

EXAMPLE 3

Preparation of an Immunogenic Composition Against Human Cytomegalovirus Infections Immunogenic compositions comprising, as vaccine antigen, a recombinant protein derived from an envelope glycoprotein of the Cytomegalovirus (CMV) Towne strain, called gB, the nucleotide and protein sequences of which are described in U.S. Pat. No. 5,834,307, were prepared. This recombinant protein was produced by a recombinant CHO line transfected with a plasmid called pPRgB27clv4 which contained a modified gB gene. Specifically, in order to facilitate the production of this recombinant protein by the CHO line, the gB gene was modified beforehand by deleting the part of the gene that encodes the transmembrane region of the gB protein corresponding to the amino acid sequence between Valine 677 and Arginine 752 and by introducing 3 point mutations such that the cleavage site that exists in the native gB was eliminated. In fact, the recombinant protein produced by the recombinant CHO line corresponds to a truncated gB protein devoid of cleavage site and of transmembrane region, called gBd™.

The construction of the plasmid pPRgB27clv4 and the production of the truncated gB protein (gBd™) by the recombinant CHO line are described in U.S. Pat. No. 6,100,064. The purification of the truncated gB protein was carried out on an immunoaffinity chromatographic column using the monoclonal antibody 15D8 described by Rasmussen L. et al. (J. Virol. (1985) 55: 274-280).

From a stock composition at 0.975 mg/ml of gB antigen thus obtained and maintained in phosphate buffer, the emulsion according to the invention concentrated as described in example 1, and an emulsion of the prior art obtained by microfluidization, 50 µl doses of immunizing compositions were prepared, having the following compositions:

2 µg of gB in citrate buffer at pH 6 (group called gB alone),
2 µg of gB; 1.075 mg of squalene; 0.133 mg of Montane™ VG 85 and 0.125 mg of Tween™80 in citrate buffer at pH 6 (group called <<with emulsion of the prior art>>),
2 µg of gB; 1.25 mg of squalene; 0.185 mg of Dehymuls SMO; 0.235 mg of Eumulgin™ B1 and 0.230 mg of mannitol in PBS buffer at pH 7.4 (group called <<with emulsion of the invention>>).

Three groups of ten 8-week-old female Outbred OF1 mice were immunized twice, on D0 and on D21, subcutaneously, with one of the compositions indicated above (each group of mice was given the same composition both times).

Blood samples were taken from the retroorbital sinus on D20 and D34 and were used to determine the concentrations of IgG1- and IgG2a-type antibodies specific for the gB antigen. The assays were carried out by means of ELISA assays; the results obtained are given in the table below, and are expressed as $\log_{10}$ of the ELISA titers. The values indicated are the mean values obtained for each group of mice.

| Nature of the groups | D20 | | D34 | | IgG1/IgG2a ratio at D34 |
|---|---|---|---|---|---|
| | IgG1 | IgG2a | IgG1 | IgG2a | |
| gB alone | 2.474 | 2.094 | 3.801 | 2.941 | 137 |
| gB + emulsion of the prior art | 4.063 | 2.980 | 5.493 | 4.185 | 143 |
| gB + emulsion according to the invention | 4.615 | 3.914 | 5.615 | 4.854 | 14 |

These results show the effectiveness of the emulsion according to the invention, which allows a greater induction of antibodies, both those of IgG1 type and of IgG2a type, with, in addition, compared with the emulsion according to the prior art, the obtaining of the desired result in the context of a vaccine against human cytomegalovirus, which is that of orienting the immune response toward a TH1 response (an indicator of which is the IgG2a titer), while at the same time maintaining the TH2-type response (an indicator of which is the IgG1 titer) at a sufficient level.

EXAMPLE 4

Immunogenic Composition Against the Flu

Flu virus antigens were obtained according to the process described in the examples of application WO 96/05294, with the exception that the viral strain used was the A/New Caledonia H1N1 strain.

Using this preparation of antigens, the concentrated emulsion according to the invention obtained in example 1, and a suspension of aluminum provided by REHEIS under the name AlOOH Rehydra, 50 µl immunization doses were prepared, which doses had the composition indicated hereinafter, in which the amounts of flu antigens are expressed by weight of hemagglutinin HA:

either 1 µg of HA in PBS buffer,
or 5 µg of HA in PBS buffer,
or 1 µg of HA and 60 µg of aluminum hydroxide,
or 1 µg of HA; 1.25 mg of squalene; 0.185 mg of Dehymuls™ SMO; 0.235 mg of Eumulgin™ B; 0.21 mg of mannitol; the entire mixture in PBS buffer.

Eight groups of five 8-week-old female BALB/c mice were administered, on D0, with the compositions prepared according to the following distribution:

one group received the composition having 1 µg of HA, subcutaneously,
one group received the same composition having 1 µg of HA, intradermally,
one group received the composition having 5 µg of HA, subcutaneously,
one group received the same composition having 5 µg of HA, intradermally,
one group received the composition having 1 µg of HA and 60 µg of aluminum, subcutaneously,
one group received the same composition having 1 µg of HA and 60 µg of aluminum, intradermally,
one group received the composition having 1 µg of HA and the emulsion according to the invention, subcutaneously,
one group received the composition having 1 µg of HA and the emulsion according to the invention, intradermally.

Blood samples were taken from each of the mice on D14, D28, D41, D56 and D105.

The sera from the immunized mice were assayed first by the ELISA technique in order to evaluate their content of total antibodies induced against the flu strain A/H1N1 of the trivalent vaccine. The antibody titers are expressed as the log10 value of arbitrary ELISA units, with a detection threshold of 1.3 log10.

These sera were the assayed by the HAI (hemaglutination inhibition) technique in order to determine their content of functional antibodies against the flu strain A/H1N1. The antibody titers are expressed as the inverse of the dilution in arithmetic value, with a detection threshold at 5.

The results obtained are reiterated in the tables hereinafter, in which the values indicated represent the mean of the titers of the mice of each group.

ELISA Titers:

| Group of mice | Immunization route | D14 | D28 | D41 | D56 | D105 |
|---|---|---|---|---|---|---|
| HA 1 µg | subcutaneous | 2.838 | 3.288 | 3.556 | 3.581 | 3.535 |
| HA 5 µg | subcutaneous | 3.203 | 3.642 | 3.836 | 3.732 | 3.844 |
| HA 1 µg + AlOOH | subcutaneous | 2.860 | 3.363 | 3.843 | 3.951 | 3.982 |
| HA 1 µg + emulsion | subcutaneous | 4.043 | 4.511 | 4.753 | 4.723 | 4.681 |
| HA 1 µg | intradermal | 2.174 | 2.814 | 3.143 | 3.075 | 2.735 |
| HA 5 µg | intradermal | 2.839 | 3.297 | 3.496 | 3.549 | 3.479 |
| HA 1 µg + AlOOH | intradermal | 2.654 | 3.004 | 3.137 | 3.020 | 2.724 |
| HA 1 µg + emulsion | intradermal | 4.134 | 4.692 | 4.895 | 4.911 | 4.823 |

HAI Titers:

| Group of mice | Immunization route | D14 | D28 | D41 | D56 | D105 |
|---|---|---|---|---|---|---|
| HA 1 µg | subcutaneous | 5 | 6 | 5 | 40 | 23 |
| HA 5 µg | subcutaneous |  | 5 | 9 | 20 |  |
| HA 1 µg + AlOOH | subcutaneous | 5 | 15 | 23 | 121 | 160 |
| HA 1 µg + emulsion | subcutaneous | 6 | 160 | 368 | 422 | 485 |
| HA 1 µg | intradermal | 5 | 5 | 5 | 23 | 8 |
| HA 5 µg | intradermal |  | 5 | 8 | 10 |  |
| HA 1 µg + AlOOH | intradermal | 5 | 5 | 5 | 26 | 7 |
| HA 1 µg + emulsion | intradermal | 7 | 557 | 1640 | 1557 | 1844 |

These results show the advantage of the present invention; specifically, aluminum hydroxide, which is a well known adjuvant widely used in the prior art, does not make it possible to increase the immunogenicity of the flu antigens with the same rapidity and the same strength as the formulation according to the invention; it is also noted that the composition according to the invention is particularly effective, whether given subcutaneously or intradermally.

EXAMPLE 5

Immunogenic Composition Against the Flu

The intention of this experiment was to evaluate in mice the advantage of the present invention for decreasing the amount of vaccine antigen when the vaccine involved is a vaccine against the flu which contains 3 flu virus strains as antigens and which would be administered intradermally.

To this end, the concentrated emulsion of example 1 was diluted with PBS buffer in order to obtain a 5% squalene emulsion, which was further diluted by half with a composition comprising the antigens.

A composition comprising flu virus originating from 3 different viral strains obtained in the manner described in patent application WO 96/05294 was used, the 3 strains being in this case the A/New Calcdonia (H1N1) strain, the A/Wyoming (H3N2) strain and the B/Jiangsu strain. Such a trivalent vaccine composition is conventional for a flu vaccine and corresponds to the vaccine sold in the northern hemisphere during the 2004 flu campaign. The amounts of antigens of each of the viral strains were assessed through their amount of hemagglutinins HA.

The immunization doses prepared, having a volume of 50 µl, have the compositions indicated below:

0.33 µg of HA of each of the viral strains in PBS buffer at pH 7.4;

1.31 µg of HA of each of the viral strains in PBS buffer at pH 7.4;

5.25 µg of HA of each of the viral strains in PBS buffer at pH 7.4;

10.5 µg of HA of each of the viral strains in PBS buffer at pH 7.4;

21 µg of HA of each of the viral strains in PBS buffer at pH 7.4;

0.33 µg of HA of each of the viral strains; 1.25 mg of squalene; 0.185 mg of Dehymuls™ SMO; 0.235 mg of Eumulgin™ B1 and 0.230 mg of mannitol in PBS buffer at pH 7.4;

1.31 µg of HA of each of the viral strains; 1.25 mg of squalene; 0.185 mg of Dehymuls™ SMO; 0.235 mg of Eumulgin™ B1 and 0.230 mg of mannitol in PBS buffer at pH 7.4;

5.25 µg of HA of each of the viral strains; 1.25 mg of squalene; 0.185 mg of Dehymuls™ SMO; 0.235 mg of Eumulgin™ B1 and 0.230 mg of mannitol in PBS buffer at pH 7.4.

Eight groups of ten 6- to 8-week-old female BALB/c mice were administered intradermally (internal face of the ear) with one of the compositions prepared at a rate of one composition per group.

Three weeks after immunization blood samples were taken, and for each of the groups the IgGs induced against each of the viral strains were assayed by ELISA. A hemagglutinin inhibition assay against each viral strain was also carried out for each of the groups.

The results obtained are represented in the table below in the form of means for each of the groups. The ELISA results are expressed as $\log_{10}$ of arbitrary units, and the HAI results are the mean arithmetic titers of the inverses of the dilutions.

| Nature | H1N1 | | H3N2 | | B | |
|---|---|---|---|---|---|---|
| Composition | ELISA | HAI | ELISA | HAI | ELISA | HAI |
| 0.33 µg HA | 3.51 | 35 | 4.38 | 243 | 4.28 | 25 |
| 1.31 µg HA | 3.96 | 65 | 4.74 | 640 | 4.35 | 32 |
| 5.25 µg HA | 4.16 | 92 | 5.05 | 970 | 4.62 | 53 |
| 10.5 µg HA | 4.38 | 197 | 5.18 | 1810 | 4.71 | 130 |
| 21 µg HA | 4.63 | 260 | 5.37 | 2389 | 4.98 | 184 |
| 0.33 µg HA + emulsion | 4.27 | 226 | 5.20 | 2389 | 4.91 | 149 |
| 1.31 µg HA + emulsion | 4.46 | 279 | 5.37 | 3880 | 4.95 | 171 |
| 5.25 µg HA + emulsion | 4.68 | 394 | 5.58 | 5487 | 5.12 | 2a2 |

These results make it possible to demonstrate the particular advantage of the invention for reducing the amount of antigens; specifically, by virtue of the emulsion according to the invention, it is possible, for the same immune response induced, to very substantially decrease the amount of antigens present in the immunization dose.

EXAMPLE 6

Trivalent Vaccine Composition Against the Flu in a Non-Naive Population

The intention of this experiment was to test the effectiveness of the emulsion of the invention in the case of a flu vaccine that would be administered to individuals whose body has already been in contact with flu virus antigens, as is frequently the case, either because the individuals have already been in contact with the flu virus, or because they have already been previously immunized with a flu vaccine.

According to the information published by C. W. Potter in *Vaccine*, 2003, 21:940-5, it is possible to use BALB/c mice pre-immunized intramuscularly with a trivalent vaccine as animal model for carrying out this test.

50 μl immunization doses comprising either PBS buffer only, or trivalent vaccine from the 2004 campaign, i.e., a vaccine comprising the A/New Calcdonia (H1N1) strain, the A/Wyoming (H3N2) strain and the B/Jiangsu strain, in a proportion of 5 μg of HA of each of the strains, in PBS buffer at pH 7.4, were prepared.

Six groups of seven BALB/c mice were provided; 3 groups were immunized with the doses comprising only buffer, and 3 others with the trivalent vaccine, intramuscularly.

30 μl immunization doses were also prepared from the concentrated emulsion of example 1 and a vaccine composition comprising the 3 viral strains of the 2004 campaign mentioned above, these immunization doses had the following compositions:

PBS buffer alone,
0.3 μg of HA of each of the viral strains in PBS buffer,
0.3 μg of HA of each of the viral strains; 0.75 mg of squalene; 0.11 mg of Dehymuls™ SMO; 0.143 mg of Eumulgin™ B1 and 0.138 mg of mannitol in PBS buffer at pH 7.4.

Each of the compositions thus prepared was used to immunize, on D34 intradermally (in the internal face of the ear), both a group of mice having previously received only PBS buffer, and a group of mice having received a dose of trivalent vaccine.

On D56, a blood sample was taken from each of the mice and the antibodies produced against the H1N1 strain (A/New Calcdonia) were titered by means of a hemagglutinin inhibition assay.

The results obtained are summarized in the table below and represent the mean values obtained for each group of mice having followed the same immunization protocol.

| Mouse group identification | Nature of the dose for the im priming | Nature of the dose for the id boost | HAI titer with respect to the H1N1 strain |
|---|---|---|---|
| A | PBS | PBS | 5 |
| B | PBS | Trivalent vaccine containing 0.3 μg HA/strain | 59 |
| C | PBS | Trivalent vaccine containing 0.3 μg HA/strain + emulsion | 320 |
| D | Trivalent vaccine containing 5 μg HA/strain | PBS | 145 |
| E | Trivalent vaccine containing 5 μg HA/strain | Trivalent vaccine containing 0.3 μg HA/strain | 476 |
| F | Trivalent vaccine containing 5 μg HA/strain | Trivalent vaccine containing 0.3 μg HA/strain + emulsion | 861 |

These results show how advantageous the invention is, even in individuals who are non-naïve with respect to the antigen administered. In fact, contrary to the observations by C. W. Potter when using this model, who, himself, has only been able to show a weak adjuvant effect of Iscoms when they were used to immunize mice pre-infected or pre-immunized with flu antigens, here it is seen that the emulsion according to the invention makes it possible to significantly increase the response induced, whether the mice immunized are naïve mice or mice having already been immunized with flu vaccine.

EXAMPLE 7

Trivalent Vaccine Composition Against the Flu Comprising Low Doses of Antigens

30 μl immunization doses were prepared from the concentrated emulsion of example 1 and a vaccine composition comprising the 3 viral strains of the 2004 campaign (the A/New Calcdonia (H1N1) strain, the A/Wyoming (H3N2) strain and the B/Jiangsu strain), these immunization doses having the following compositions:

0.1 μg of HA of each of the viral strains in PBS buffer,
0.4 μg of HA of each of the viral strains in PBS buffer,
1.6 μg of HA of each of the viral strains in PBS buffer,
6.3 μg of HA of each of the viral strains in PBS buffer,
0.1 μg of HA; 0.75 mg of squalene; 0.11 mg of Dehymuls™ SMO; 0.143 mg of Eumulgin™ B1 and 0.138 mg of mannitol in PBS buffer at pH 7.4,
0.4 μg of HA; 0.75 mg of squalene; 0.11 mg of Dehymuls™ SMO; 0.143 mg of Eumulgin™ B1 and 0.138 mg of mannitol in PBS buffer at pH 7.4.

Six groups of eight 8-week-old female BALB/c mice were administered on D0 intradermally (internal face of the ear) a dose of 30 μl of one of the compositions indicated below (1 composition per group).

In each group, a 2nd dose having the same nature as the 1st dose administered was again administered intradermally to half the mice on D29.

Blood samples were taken on D22 and on D43 in order to determine the amounts of antibodies induced.

The antibody titers were assayed by ELISA for the antibodies induced at D22 and at D43, with respect to all the strains administered: H1N1, H3N2 and B, and by HAI with respect to the H1N1 strain only, both at D22 and at D43. The results obtained are summarized in the table below, in which the titers expressed are the means obtained for each group of mice. As regards the results at D43, the means were determined separately within the same group, for the mice having received 2 doses of vaccine and those having received only one.

| Vaccine composition | H1N1 ELISA titer at D22 | H3N2 ELISA titer at D22 | B ELISA titer at D22 | H1N1 HAI titer at D22 | H1N1 HAI titer at D43 Boosted mice | H1N1 HAI titer at D43 Non-boosted mice |
|---|---|---|---|---|---|---|
| 0.1 μg HA | 3.467 | 4.131 | 4.063 | 57 | 95 | 80 |
| 0.4 μg HA | 3.816 | 4.527 | 4.313 | 73 | 226 | 80 |

-continued

| | | | | | | |
|---|---|---|---|---|---|---|
| 1.6 µg HA | 4.069 | 4.831 | 4.750 | 147 | 1280 | 135 |
| 6.3 µg HA | 4.534 | 5.298 | 4.947 | 320 | 1522 | 320 |
| 0.1 µg HA + emulsion | 4.200 | 5.015 | 4.807 | 207 | 2153 | 538 |
| 0.4 µg HA + emulsion | 4.612 | 5.482 | 5.001 | 453 | 2560 | 640 |

| Vaccine composition | H1N1 ELISA titer at D43 | | H3N2 ELISA titer at D43 | | B ELISA titer at D43 | |
|---|---|---|---|---|---|---|
| | Boosted mice | Non-boosted mice | Boosted mice | Non-boosted mice | Boosted mice | Non-boosted mice |
| 0.1 µg HA | 3.833 | 3.425 | 4.782 | 4.174 | 4.479 | 3.911 |
| 0.4 µg HA | 4.385 | 3.599 | 5.250 | 4.354 | 5.053 | 4.079 |
| 1.6 µg HA | 4.906 | 3.876 | 5.526 | 4.779 | 5.458 | 4.487 |
| 6.3 µg HA | 5.287 | 4.176 | 6.073 | 5.033 | 5.678 | 4.773 |
| 0.1 µg HA + emulsion | 5.210 | 4.523 | 5.990 | 5.264 | 5.723 | 4.943 |
| 0.4 µg HA + emulsion | 5.394 | 4.790 | 6.171 | 5.640 | 5.962 | 5.144 |

These results show that, by virtue of the emulsion according to the invention, even with low doses of antigens, very substantial humoral responses are obtained. Thus, the results obtained with only 0.4 µg of HA of each of the viral strains, much better responses are obtained by using the emulsion according to the invention than by using a dose of 6.3 µg of HA alone. In addition, it is noted that, even in the individuals not given a booster dose, the immune system continues to induce antibodies, whereas this is not the case for the individuals given the non-adjuvanted vaccine antigens.

EXAMPLE 8

Trivalent Vaccine Composition Against the Flu

30 µl immunization doses were prepared from the concentrated emulsion of example 1 and a vaccine composition comprising the 3 viral strains of the 2004 campaign (the A/New Calcdonia (H1N1) strain, the A/Wyoming (H3N2) strain and the B/Jiangsu strain), these immunization doses having the following compositions:

0.1 µg of HA of each of the viral strains in PBS buffer, 0.4 µg of HA of each of the viral strains in PBS buffer, 1.6 µg of HA of each of the viral strains in PBS buffer, 6.3 µg of HA of each of the viral strains in PBS buffer, 0.1 µg of HA; 0.75 mg of squalene; 0.11 mg of Dehymuls™ SMO; 0.143 mg of Eumulgin™ B1 and 0.138 mg of mannitol in PBS buffer at pH 7.4, 0.4 µg of HA; 0.75 mg of squalene; 0.11 mg of Dehymuls™ SMO; 0.143 mg of Eumulgin™ B1 and 0.138 mg of mannitol in PBS buffer at pH 7.4.

Six groups of eight 8-week-old female C57BL/6J mice were administered on D0 intradermally (internal face of the ear) a dose of 30 µl of one of the compositions indicated above (1 composition per group).

Blood samples were taken on D23 in order to determine the amounts of antibodies induced.

The antibody titers were assayed by ELISA and by HAI for the antibodies induced with respect to all the strains administered: H1N1, H3N2 and B.

The results obtained are summarized in the table below, in which the titers expressed are the means obtained for each group of mice.

| Composition | ELISA H1N1 | ELISA H3N2 | ELISA B | HAI H1N1 | HAI H3N2 | HAI B |
|---|---|---|---|---|---|---|
| 0.1 µg HA | 2.924 | 3.506 | 3.920 | 26 | 174 | 95 |
| 0.4 µg HA | 3.673 | 4.227 | 4.431 | 135 | 269 | 147 |
| 1.6 µg HA | 3.948 | 4.593 | 4.786 | 160 | 381 | 190 |
| 6.3 µg HA | 4.446 | 5.106 | 5.190 | 587 | 1174 | 453 |
| 0.1 µg HA + emulsion | 4.456 | 5.192 | 5.064 | 349 | 1974 | 320 |
| 0.4 µg HA + emulsion | 4.659 | 5.337 | 5.174 | 761 | 2348 | 494 |

Again, the results obtained show the great advantage of the emulsion according to the invention, by virtue of which it is possible to very substantially reduce the amounts of antigens present. Specifically, it can be considered, overall, that with only 0.1 µg of HA adjuvanted with the emulsion according to the invention, results are obtained that are as good as with an amount of 6.3 µg of HA.

EXAMPLE 9

Trivalent Vaccine Composition Against the Flu Comprising an Emulsion According to the Invention or According to the Prior Art 30 µl immunization doses were prepared from the concentrated emulsion of example 1 and a vaccine composition comprising the 3 viral strains of the 2004 campaign (the A/New Calcdonia (H1N1) strain, the A/Wyoming (H3N2) strain and the B/Jiangsu strain), these immunization doses having the following compositions:

0.3 µg of HA of each of the viral strains in PBS buffer, 6.3 µg of HA of each of the viral strains in PBS buffer, 0.3 µg of HA; 0.21 mg of squalene; 0.031 mg of Dehymuls™ SMO; 0.040 mg of Eumulgin™ B1 and 0.039 mg of mannitol in PBS buffer at pH 7.4 (emulsion at 0.7%), 0.3 µg of HA; 0.75 mg of squalene; 0.11 mg of Dehymuls™ SMO; 0.143 mg of Eumulgin™ B1 and 0.138 mg of mannitol in PBS buffer at pH 7.4 (emulsion at 2.5%), 0.3 µg of HA; 0.645 mg of squalene; 0.075 mg of Tween™ 80; 0.075 mg of Span™ 85 (emulsion according to the prior art obtained by microfluidization).

Five groups of eight 8-week-old female BALB/c mice were administered on D0 intradermally (internal face of the ear) a dose of 30 µl of one of the compositions indicated above (1 composition per group).

To evaluate the amount of antibodies induced, blood samples were taken on D21 and the activity against the A/H1N1 strain, the A/H3N2 strain and the B strain was determined on said blood samples by HAI (hemagglutination inhibition).

The results obtained for each group of mice are represented in the table below.

| Composition tested | HAI against H1N1 | HAI against H3N2 | HAI against B |
|---|---|---|---|
| 0.3 µg HA | 26 | 174 | 8 |
| 6.3 µg HA | 247 | 905 | 73 |
| 0.3 µg HA + invention emulsion at 0.7% | 95 | 640 | 37 |
| 0.3 µg HA + invention emulsion at 2.5% | 269 | 1974 | 73 |
| 0.3 µg HA + prior art emulsion | 135 | 987 | 57 |

These results show that, with an emulsion obtained according to the invention by virtue of a very simple preparation process consisting of phase inversion by means of a change in temperature, an adjuvant is obtained which is as good as, and even slightly better than, the emulsion of the prior art obtained using very high shear rates.

EXAMPLE 10

Trivalent Vaccine Composition Against the Flu Comprising an Emulsion According to the Invention at Various Concentrations 30 µl immunization doses were prepared from the concentrated emulsion of example 1 and a vaccine composition comprising the 3 viral strains of the 2004 campaign (the A/New Calcdonia (H1N1) strain, the A/Wyoming (H3N2) strain and the B/Jiangsu strain), these immunization doses having the following compositions:
  0.3 µg of HA of each of the viral strains in PBS buffer,
  6.3 µg of HA of each of the viral strains in PBS buffer,
  0.3 µg of HA of each of the viral strains; 0.12 mg of squalene; 0.018 mg of DehyMuls™ SMO; 0.023 mg of Eumulgin™ B1 and 0.022 mg of mannitol in PBS buffer at pH 7.4 (emulsion at 0.4%),
  0.3 µg of HA of each of the viral strains; 0.299 mg of squalene; 0.044 mg of Dehymuls™ SMO; 0.057 mg of Eumulgin™ B1 and 0.055 mg of mannitol in PBS buffer at pH 7.4 (emulsion at 1%),
  0.3 µg of HA of each of the viral strains; 0.75 mg of squalene; 0.11 mg of Dehymuls™ SMO; 0.143 mg of Eumulgin™ B1 and 0.138 mg of mannitol in PBS buffer at pH 7.4 (emulsion at 2.5%).

Five groups of eight 8-week-old female BALB/c mice were administered on D0 intradermally (internal face of the ear) a dose of 30 µl of one of the compositions indicated above (1 composition per group).

In order to evaluate the amount of antibodies induced, blood samples were taken at D21 and the anti-H1N1 antibodies, the anti-H3N2 antibodies and the anti-B antibodies were determined on these blood samples by ELISA, and the activity against the A/H1N1 strain, the A/H3N2 strain and the B strain is determined by HAI (hemagglutination inhibition).

The results obtained are represented in the table below in the form of means for each of the groups; the ELISA results are expressed in $\log_{10}$ of arbitrary ELISA units and the HAI results are the mean arithmetic titers of the inverses of dilutions.

| Composition tested | Anti-H1N1 | | Anti-H3N2 | | Anti-B | |
|---|---|---|---|---|---|---|
| | ELISA | HAI | ELISA | HAI | ELISA | HAI |
| 0.3 µg HA | 3.864 | 67 | 4.594 | 320 | 4.406 | 31 |
| 6.3 µg HA | 4.478 | 269 | 5.041 | 1660 | 5.053 | 135 |
| 0.3 µg HA + invention emulsion at 0.4% | 4.053 | 108 | 4.827 | 525 | 4.545 | 54 |
| 0.3 µg HA + invention emulsion at 1% | 4.312 | 269 | 5.074 | 1174 | 4.733 | 123 |
| 0.3 µg HA + invention emulsion at 2.5% | 4.425 | 293 | 5.200 | 1974 | 4.840 | 123 |

These results confirm once again that, whatever the strain evaluated, the emulsion according to the invention makes it possible, with a very low dose of antigens, to obtain a very substantial immune system response.

EXAMPLE 11

Preparation of a Lyophilizable Composition

The process described in example 1 was carried out using water instead of the buffer; the emulsion obtained was subsequently diluted with an aqueous solution comprising mannitol, sucrose and dodecylmaltoside, in order to obtain an emulsion whose final composition is as follows:
  5% of squalene,
  0.95% of polyoxyethylene cetostearyl ether,
  0.75% of sorbitan monooleate
  3% of mannitol,
  2% of dodecylmaltoside,
  6% of sucrose.

This emulsion was lyophilized and conserved at 4° C. for 3 months; then, after reconstitution, it was noted that its properties were conserved, in particular its monodisperse emulsion qualities, with d50 and d90 values close to those measured before lyophilization.

This emulsion can be diluted 50/50 with a solution comprising vaccine antigens in order to obtain a vaccine composition.

EXAMPLE 12

Comparison of the Adjuvant Effect of the Emulsion According to the Invention and of a Surfactant Present in the Emulsion The intention of this experiment was to evaluate the adjuvant activity of the emulsion according to the invention, compared with that of the surfactant Eumulgin™ B1 which is present in the emulsion.

For this, a test was carried out on mice using flu antigens.

To this end, flu virus antigens obtained according to the process described in the examples of application WO 96/05294 were used, with the exception that the viral strain used was the A/New Calcdonia H1N1 strain. A vaccine composition comprising the 3 viral strains of the 2004 campaign (the A/New Calcdonia (H1N1) strain, the A/Wyoming (H3N2) strain and the B/Jiangsu strain) was used.

100 µl immunization doses were prepared from the concentrated emulsion obtained according to the invention and described in example 1, from Eumulgin™ B1, and from the flu virus antigen compositions, these immunization doses having the following compositions:

1 µg of HA of the H1N1 strain in PBS buffer at pH 7.4;
5 µg of HA of the H1N1 strain in PBS buffer at pH 7.4;
1 µg of HA of the H1N1 strain; 2.5 mg of squalene; 0.37 mg of Dehymuls™ SMO; 0.48 mg of Eumulgin™ B1 and 0.46 mg of mannitol in PBS buffer at pH 7.4;
1 µg of HA of the H1N1 strain and 0.48 mg of Eumulgin™ B1 in PBS buffer at pH 7.4;
0.33 µg of HA of each of the viral stains in PBS buffer at pH 7.4;
1.66 µg of HA of each of the viral stains in PBS buffer at pH 7.4;
0.33 µg of HA of each of the viral stains; 2.5 mg of squalene; 0.37 mg of Dehymuls™ SMO; 0.48 mg of Eumulgin™ B1 and 0.46 mg of mannitol in PBS buffer at pH 7.4;
0.33 µg of HA of each of the viral stains and 0.48 mg of Eumulgin™ B1 in PBS buffer at pH 7.4.

Eight groups of 8 female BALB/c mice were immunized by means of a single intramuscular injection on D0. Blood samples were taken on D21 and D35 in order to evaluate by ELISA assay their content of total antibodies induced against the A/H1N1 flu strain or against each of the strains of the trivalent vaccine. The antibody titers, indicated in the table below, are expressed as the log10 value of arbitrary ELISA units, with a detection threshold of 1.3 log10.

| Immunization dose compositions | Titers at D21 | | | Titers at D35 | | |
|---|---|---|---|---|---|---|
| | H1N1 | H3N2 | B | H1N1 | H3N2 | B |
| H1N1 at 1 µg | 2.745 | | | 2.848 | | |
| H1N1 at 5 µg | 3.057 | | | 3.139 | | |
| H1N1 at 1 µg + invention emulsion | 4.002 | | | 4.128 | | |
| H1N1 at 1 µg + Eumulgin ™ B1 | 3.019 | | | 3.119 | | |
| Trivalent vaccine at 1 µg of total HA | 3.111 | 3.718 | 3.706 | 3.218 | 4.147 | 3.935 |
| Trivalent vaccine at 5 µg of total HA | 3.692 | 4.386 | 3.975 | 3.776 | 4.632 | 4.225 |
| Trivalent vaccine at 1 µg of total HA + invention emulsion | 4.252 | 5.002 | 4.596 | 4.186 | 5.214 | 4.897 |
| Trivalent vaccine at 1 µg of total HA + Eumulgin ™ B1 | 3.146 | 3.712 | 3.950 | 3.241 | 4.177 | 4.242 |

The results obtained in this test confirm those already obtained in previous tests, namely that the emulsion according to the invention makes it possible to greatly reduce the dose of antigens for the same immune system response; a better response is in fact obtained using the emulsion according to the invention with only 1 µg of HA rather than using a dose of 5 µg of HA without adjuvant.

It is also observed that the surfactant used does not really exhibit any adjuvant effect when it is used alone, whereas the emulsion according to the invention itself produces a highly adjuvant effect with respect to all the strains tested.

What is claimed is:

1. An oil-in-water adjuvant emulsion which comprises:
i) squalene,
ii) an aqueous solvent,
iii) a polyoxyethylene alkyl ether hydrophilic nonionic surfactant, and
iv) a hydrophobic nonionic surfactant,
wherein the emulsion is thermoreversible and wherein 90% of the population by volume of the oil drops has a size less than 200 nm.

2. The emulsion of claim 1 wherein the polyoxyethylene alkyl ether is of formula $CH_3-(CH_2)_x-(O-CH_2-CH_2)_n-OH$, in which n is an integer from 10 to 60, and x is an integer from 11 to 17.

3. The emulsion as claimed in claim 1, wherein 90% of the population by volume of the oil drops has a size less than 160 nm.

4. The emulsion as claimed in claim 3, wherein 90% of the population by volume of the oil drops has a size less than 150 nm.

5. The emulsion as claimed in claim 1, wherein 50% of the population by volume of the oil drops has a size less than 100 nm.

6. The emulsion as claimed in claim 5, wherein 50% of the population by volume of the oil drops has a size less than 90 nm.

7. The emulsion according to claim 1, which also comprises at least one alditol.

8. The emulsion as claimed in claim 1, wherein the hydrophobic nonionic surfactant is a sorbitan ester or mannide ester surfactant.

9. The emulsion according to claim 1, wherein the polyoxyethylene alkyl ether surfactant is polyoxyethylene(12) cetostearyl ether.

10. The emulsion according to claim 7, wherein the alditol is chosen from glycerol, erythritol, xylitol, sorbitol and mannitol.

11. The emulsion according to claim 1, wherein the hydrophobic nonionic surfactant is sorbitan monooleate.

12. The emulsion according to claim 1, wherein the amount of squalene is between 5 and 45%.

13. The emulsion according to claim 1, wherein the amount of polyoxyethylene alkyl ether surfactant is between 0.9 and 9%.

14. The emulsion according to claim 1, wherein the amount of hydrophobic nonionic surfactant is between 0.7 and 7%.

15. The adjuvant emulsion according to claim 1, which comprises:
i) 32.5% of squalene,
ii) 6.18% of polyoxyethylene(12) cetostearyl ether,
iii) 4.82% of sorbitan monooleate, and
iv) 6% of mannitol.

16. The emulsion according to claim 1, which also comprises an alkylpolyglycoside.

17. The emulsion according to claim 1, which also comprises a cryoprotective agent.

18. A process for preparing an immunogenic composition comprising at least one vaccine antigen and a squalene-containing oil-in-water emulsion, the process comprising making the squalene-containing oil-in-water emulsion according to claim 1 by a phase-inversion temperature process.

19. The process as claimed in claim 18, wherein the oil-in-water emulsion is prepared by cooling a water-in-oil inverse emulsion which comprises:
i) squalene,
ii) an aqueous solvent,
iii) a polyoxyethylene alkyl ether hydrophilic nonionic surfactant, and
iv) a hydrophobic nonionic surfactant.

20. The process as claimed in claim 19, wherein the water-in-oil inverse emulsion is prepared by mixing squalene, an aqueous solvent, a polyoxyethylene alkyl ether hydrophilic nonionic surfactant, and a hydrophobic nonionic surfactant to obtain a coarse oil-in-water emulsion, and then heating the emulsion to at least its phase inversion temperature in order to obtain an inverse emulsion.

21. The process as claimed in claim 19, wherein the water-in-oil inverse emulsion is prepared by:
separately heating (a) the aqueous phase comprising the aqueous solvent and the polyoxyethylene alkyl ether nonionic surfactant and (b) the oily phase comprising the squalene and the hydrophobic surfactant, and
mixing the pre-heated aqueous and oily phases.

22. The process as claimed in claim 21, wherein:
the aqueous and oily phases are heated, separately, to a temperature below the phase inversion temperature of the emulsion,
the two phases are mixed to obtain an oil-in-water emulsion,
the oil-in-water emulsion obtained is then heated to a temperature at least equal to the phase inversion temperature of the emulsion, in order to obtain a water-in-oil inverse emulsion.

23. The process as claimed in claim 18, wherein the phase inversion temperature is between 45 and 80° C.

24. The process as claimed in claim 23, wherein the phase inversion temperature is between 50 and 65° C.

25. The process as claimed in claim 18, which also comprises at least one lyophilization step.

26. An immunogenic composition prepared according to the process of claim 18.

27. An immunogenic composition comprising an antigen and an emulsion according to claim 1.

* * * * *